United States Patent
Aida et al.

(10) Patent No.: US 10,400,047 B2
(45) Date of Patent: Sep. 3, 2019

(54) OLEFIN POLYMERIZATION CATALYST AND METHOD FOR PRODUCING OLEFIN OLIGOMER

(71) Applicant: JXTG NIPPON OIL & ENERGY CORPORATION, Tokyo (JP)

(72) Inventors: Fuyuki Aida, Tokyo (JP); Kazuo Tagawa, Tokyo (JP)

(73) Assignee: JXTG NIPPON OIL & ENERGY CORPORATION, Tokyo (JP)

(*) Notice: Subject to any disclaimer, the term of this patent is extended or adjusted under 35 U.S.C. 154(b) by 0 days.

(21) Appl. No.: 15/553,310

(22) PCT Filed: Feb. 25, 2016

(86) PCT No.: PCT/JP2016/055668
§ 371 (c)(1),
(2) Date: Aug. 24, 2017

(87) PCT Pub. No.: WO2016/136892
PCT Pub. Date: Sep. 1, 2016

(65) Prior Publication Data
US 2018/0016367 A1    Jan. 18, 2018

(30) Foreign Application Priority Data
Feb. 27, 2015  (JP) .................. 2015-038588

(51) Int. Cl.
| | | |
|---|---|---|
| C08F 10/02 | (2006.01) | |
| C07F 15/00 | (2006.01) | |
| C07F 15/04 | (2006.01) | |
| C08F 110/02 | (2006.01) | |
| C07C 2/32 | (2006.01) | |

(52) U.S. Cl.
CPC .......... *C08F 10/02* (2013.01); *C07C 2/32* (2013.01); *C07F 15/0066* (2013.01); *C07F 15/045* (2013.01); *C08F 110/02* (2013.01); *C07C 2531/14* (2013.01); *C07C 2531/22* (2013.01)

(58) Field of Classification Search
None
See application file for complete search history.

(56) References Cited

U.S. PATENT DOCUMENTS

2007/0112150 A1    5/2007  Small et al.

FOREIGN PATENT DOCUMENTS

| CN | 101531725 A | 9/2009 |
|---|---|---|
| CN | 102432415 A | 5/2012 |
| JP | 2000-516295 A | 12/2000 |
| JP | 2002-302510 A | 10/2002 |
| JP | 2007-529616 A | 10/2007 |
| WO | 98027124 A | 6/1986 |
| WO | 2005090425 A1 | 9/2005 |

OTHER PUBLICATIONS

Walter Kaminsky, "New polymers by metallocene catalysis", Macromolecular Chemistry and Physics, 1996, p. 3907-p. 3945, vol. 197, Issue 12.

Lynda K. Johnson et al., "New Pd(II)- and Ni(II)-Based Catalysts for Polymerization of Ethylene and α-Olefins", Journal of the American Chemical Society, 1995, p. 6414-p. 6415, vol. 117, Issue 23.

Roland Schmidt et al., "Heterogenized iron(II) complexes as highly active ethene polymerization catalysts," Journal of Molecular Catalysis A: Chemical, 2002, p. 155-p. 173, vol. 179, Issues 1-2.

Christian Görl et al., "Bis(arylimino)pyridine iron(III) complexes as catalyst precursors for the oligomerization and polymerization of ethylene", Applied Catalysts A: General, 2011, p. 25-p. 35, vol. 403.

(Continued)

*Primary Examiner* — Catherine S Branch
(74) *Attorney, Agent, or Firm* — Greenblum & Bernstein, P.L.C.

(57) ABSTRACT

An olefin polymerization catalyst containing a complex of a ligand being a diimine compound represented by the formula (1) and at least one metal selected from the group consisting of Group 8 elements, Group 9 elements and Group 10 elements:

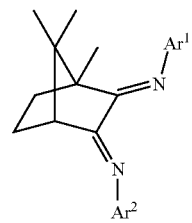

(1)

wherein $Ar^1$ and $Ar^2$ are respectively a group represented by the formula (2):

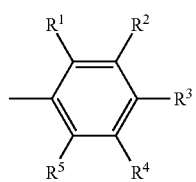

(2)

wherein $R^1$ and $R^5$ are respectively a hydrogen atom or a hydrocarbyl group having 1 to 5 carbon atoms, the total number of carbon atoms of $R^1$ and $R^5$ is 1 or more and 5 or less, and $R^2$, $R^3$ and $R^4$ are respectively a hydrogen atom or an electron-donating group.

4 Claims, No Drawings

(56) References Cited

OTHER PUBLICATIONS

Konstantin P. Bryliakov et al., "Formation and Nature of the Active Sites in Bis(imino)pyridine Iron-Based Polymerization Catalysts", Organometallics, 2009, p. 3225-p. 3232, vol. 28, Issue 11.

Daniel J. Arriola et al., "Catalytic Production of Olefin Block Copolymers via Chain Shuttling Polymerization", Science, 2006, p. 714-p. 719, vol. 312, Issue 5774.

Thomas Schleis et al., "Ni(II) and Pd(II) complexes of camphor-derived diazadiene ligands: steric bulk tuning and ethylene polymerization", Inorganic Chemistry Communications, 1998, p. 431-p. 434, vol. 1, No. 11.

Jun Liu et al., "Polymerization of α-Olefins Using a Camphyl α-Diimine Nickel Catalyst at Elevated Temperature", Macromolecules, 2014, p. 3325-p. 3331, vol. 47.

International Search Report from Patent Application No. PCT/JP2016/055668, dated Apr. 26, 2016.

International Preliminary Report on Patentability from Patent Application No. PCT/JP2016/055668 dated Aug. 29, 2017.

Written Opinion of the International Searching Authority issued from Application No. PCT/JP2016/055668 dated Apr. 26, 2017.

OLEFIN POLYMERIZATION CATALYST AND METHOD FOR PRODUCING OLEFIN OLIGOMER

TECHNICAL FIELD

The present invention relates to an olefin polymerization catalyst and method for producing an olefin oligomer.

BACKGROUND ART

As Catalysts used for the polymerization of an olefin, metallocene compounds, palladium catalysts, iron catalysts and catalysts consisting of a cobalt complex, methylaluminoxane and the like are known (Patent Literatures 1 to 3, Non Patent Literatures 1 to 5).

Further, as catalysts for producing block copolymers, diethylzinc, a metallocene compound, and a catalyst consisting of a palladium catalyst and dialkylzinc are known (Patent Literature 4, Non Patent Literature 6).

Further, as olefin polymerization catalysts for producing polyethylene, polypropylene and poly 1-hexene, an example using a special camphorquinone-derived diimine ligand and nickel is known (Non Patent Literature 7).

CITATION LIST

Patent Literature

Patent Literature 1: JP 2000-516295 A
Patent Literature 2: JP 2002-302510 A
Patent Literature 3: CN 102432415 A
Patent Literature 4: JP 2007-529616 A

Non Patent Literature

Non Patent Literature 1: "Macromol. Chem. Phys.", Vol. 197, 1996, p. 3907
Non Patent Literature 2: "J. Am. Chem. Soc.", Vol. 117, 1995, p. 6414
Non Patent Literature 3: "J. Mol. Cat. A: Chemical", Vol. 179, 2002, p. 155
Non Patent Literature 4: "Appl. Cat. A: General", Vol. 403, 2011, p. 25
Non Patent Literature 5: "Organometallics", Vol. 28, 2009, p. 3225
Non Patent Literature 6: "Science", Vol. 312, 2006, p. 714
Non Patent Literature 7: "Macromolecules", Vol. 47, 2014, p. 3325

SUMMARY OF INVENTION

Technical Problem

The present invention has an object to provide an olefin polymerization catalyst and a method for producing an olefin oligomer capable of efficiently oligomerizing a polymerizable monomer including an olefin.

Solution to Problem

The present invention provides an olefin polymerization catalyst containing a complex of a ligand being a diimine compound represented by the following formula (1) and at least one metal selected from the group consisting of Group 8 elements, Group 9 elements and Group 10 elements.

[Chemical Formula 1]

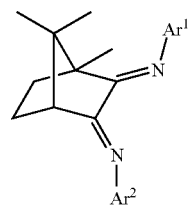

(1)

In the formula (1), $Ar^1$ and $Ar^2$ may be the same or different and are respectively a group represented by the following formula (2).

[Chemical Formula 2]

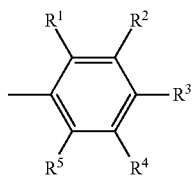

(2)

In the formula (2), $R^1$ and $R^5$ may be the same or different and are respectively a hydrogen atom or a hydrocarbyl group having 1 to 5 carbon atoms, the total number of carbon atoms of $R^1$ and $R^5$ is 1 or more and 5 or less, and $R^2$, $R^3$ and $R^4$ may be the same or different and are respectively a hydrogen atom or an electron-donating group.

The olefin polymerization catalyst can further contain an organoaluminum compound.

Further, the present invention provides a method for producing an olefin oligomer comprising a step of oligomerizing a polymerizable monomer including an olefin in the presence of the above olefin polymerization catalyst.

Advantageous Effects of Invention

According to the present invention, an olefin polymerization catalyst and a method for producing an olefin oligomer capable of efficiently oligomerizing a polymerizable monomer including an olefin can be provided.

DESCRIPTION OF EMBODIMENTS

Hereinafter, preferred embodiments of the present invention are described in detail.

[First Embodiment: Olefin Polymerization Catalyst]

The olefin polymerization catalyst according to the first embodiment of the present invention contains a complex of a ligand being a diimine compound represented by the following formula (1) and at least one metal selected from the group consisting of Group 8 elements, Group 9 elements and Group 10 elements.

[Chemical Formula 3]

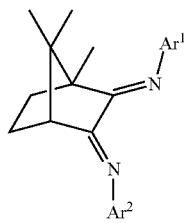

(1)

In the formula (1), $Ar^1$ and $Ar^2$ may be the same or different and are respectively a group represented by the following formula (2).

[Chemical Formula 4]

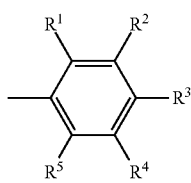

(2)

In the formula (2), $R^1$ and $R^5$ may be the same or different and are respectively a hydrogen atom or a hydrocarbyl group having 1 to 5 carbon atoms, the total number of carbon atoms of $R^1$ and $R^5$ is 1 or more and 5 or less, and $R^2$, $R^3$ and $R^4$ may be the same or different and are respectively a hydrogen atom or an electron-donating group.

Note that $Ar^1$ and $Ar^2$ in the same molecule may be the same or different but are preferably the same in light of simplifying the synthesis of the ligand.

Examples of the hydrocarbyl group having 1 to 5 carbon atoms and represented by $R^1$ and $R^5$ include an alkyl group having 1 to 5 carbon atoms and an alkenyl group having 2 to 5 carbon atoms. The hydrocarbyl group may be linear, branched or cyclic. Further, the hydrocarbyl group may be a monovalent group of a linear or branched hydrocarbyl group bonded to a cyclic hydrocarbyl group.

Examples of the alkyl group having 1 to 5 carbon atoms include a linear alkyl group having 1 to 5 carbon atoms such as a methyl group, an ethyl group, an n-propyl group, an n-butyl group and an n-pentyl group; a branched alkyl group having 1 to 5 carbon atoms such as an iso-propyl group, an iso-butyl group, a sec-butyl group, a tert-butyl group and a branched pentyl group (including all structural isomers); and a cyclic alkyl group having 1 to 5 carbon atoms such as a cyclopropyl group and a cyclobutyl group.

Examples of the alkenyl group having 2 to 5 carbon atoms include a linear alkenyl group having 2 to 5 carbon atoms such as an ethenyl group (vinyl group), an n-propenyl group, an n-butenyl group and an n-pentenyl group; a branched alkenyl group having 2 to 5 carbon atoms such as an iso-propenyl group, an iso-butenyl group, a sec-butenyl group, a tert-butenyl group and a branched pentenyl group (including all structural isomers); and acyclic alkenyl group having 2 to 5 carbon atoms such as a cyclopropenyl group, a cyclobutenyl group and a cyclopentenyl group.

In light of controlling the molecular weight of the olefin oligomer to be obtained by the olefin polymerization catalytic reaction, the total number of carbon atoms of $R^1$ and $R^5$ is 1 or more and 5 or less, preferably 1 or more and 4 or less, more preferably 1 or more and 3 or less, further preferably 1 or more and 2 or less, most preferably 1. When the total number of carbon atoms of $R^1$ and $R^5$ is within the above ranges, the production of a polymer having a large molecular weight by the olefin polymerization reaction can be reduced. Particularly, when the total number of carbon atoms of $R^1$ and $R^5$ is 5 or less, the influence of steric hindrance by a substituent on the benzene ring is reduced and the molecular conformation change easily takes place. As a result, the elimination reaction is promoted, thereby reducing the production of a polymer having a large molecular weight.

Further, in light of suppressing the influence of steric hindrance by a substituent on the benzene ring, it is preferable that either one of $R^1$ or $R^5$ be a hydrogen atom and the other be a hydrocarbyl group having 1 to 5 carbon atoms.

In the formula (2), $R^2$, $R^3$ and $R^4$ are each independently a hydrogen atom or an electron-donating group. The electron-donating group is not particularly limited and examples include an alkyl group having 1 to 8 carbon atoms, an alkoxy group having 1 to 8 carbon atoms, an aryl group, an aryloxy group and a monovalent group of two or more of these groups combined. The alkyl group and the alkoxy group may be either of linear, branched or cyclic. Further, the aryl group and the aryloxy group may have a substituent such as an alkyl group.

Examples of $R^2$, $R^3$ and $R^4$ include specifically a methyl group, an ethyl group, a linear or branched propyl group, a linear or branched butyl group, a linear or branched pentyl group, a linear or branched hexyl group, a cyclohexyl group, a methylcyclohexyl group, a phenyl group, a tolyl group, a xylyl group, a hydroxy group, a methoxy group, an ethoxy group, a linear or branched propoxy group, a linear or branched butoxy group, a linear or branched pentyloxy group, a cyclopentyloxy group, a linear or branched hexyloxy group, a cyclohexyloxy group, a phenoxy group, a tolyloxy group and a xylyloxy group. Among these, a hydrogen atom, a methyl group and a methoxy group are preferable.

Examples of the preferable aspect of the diimine compound represented by the formula (1) include each of the diimine compounds represented by the following formulae (1-1) to (1-3). These can be used singly or in combination of two or more.

[Chemical Formula 5]

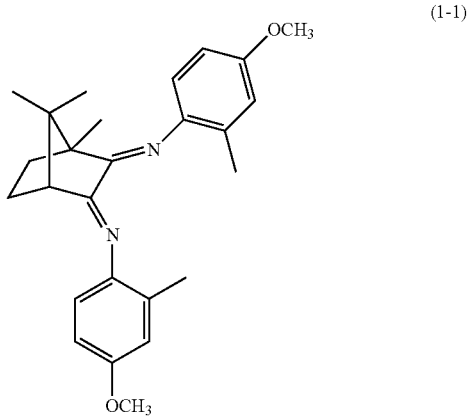

(1-1)

-continued

[Chemical Formula 6]

(1-2)

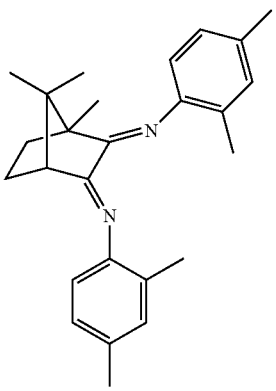

[Chemical Formula 7]

(1-3)

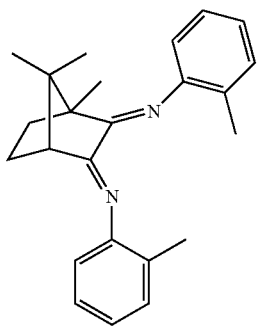

The diimine compound represented by the formula (1) can be synthesized by, for example, dehydrocondensing camphorquinone and an aniline compound in the presence of an acid.

A preferable aspect of the production method of the diimine compound represented by the formula (1) comprises a first step of dissolving camphorquinone, an aniline compound and an acid in a solvent and dehydrocondensing by heating under reflux with the solvent and a step of carrying out separation and purification treatments of the reaction mixture after the first step to obtain the diimine compound represented by the formula (1).

The acid used in the first step can be, for example, an organoaluminum compound. Examples of the organoaluminum compound include trimethylaluminum, triethylaluminum, tripropylaluminum, triisopropylaluminum, tributylaluminum, triisobutylaluminum, trihexylaluminum, trioctylaluminum, diethyl aluminum chloride, ethylaluminum chloride, ethylaluminum sesquichloride and methylaluminoxane. These organoaluminum compounds can be used singly or in combination of two or more. The amount of these organoaluminum compounds to be added is, against to camphorquinone, preferably 0.1 to 10 equivalent, more preferably 0.5 to 5 equivalent, further preferably 0.8 to 2 equivalent.

The acid used in the first step can be a protic acid in addition to the above organoaluminum compounds. The protic acid is used as a proton-donating acid catalyst. The protic acid to be used is not particularly limited but is preferably an organic acid. Examples of such a protic acid include acetic acid, trifluoroacetic acid, methanesulfonic acid, trifluoromethanesulfonic acid and para-toluenesulfonic acid. When these protic acids are used, it is preferable to remove water using a Dean-Stark water separator in light of reducing the byproduction of water. Alternatively, the reaction can also be carried out in the presence of an adsorbent such as molecular sieves. The amount of the protic acid to be added is not particularly limited and may be a catalytic amount.

Examples of the solvent used in the first step include hydrocarbon solvents and alcohol solvents. Examples of the hydrocarbon solvent include hexane, heptane, octane, benzene, toluene, xylene, cyclohexane and methylcyclohexane. Examples of the alcohol solvent include methanol, ethanol and isopropyl alcohol.

The reaction conditions for the first step can be suitably selected in accordance with the kind and amount of the raw material compounds, acid and solvent.

The separation and purification treatments in the second step is not particularly limited and examples include silica gel column chromatography and recrystallizing method. Particularly, when the organoaluminum compound described above is used as the acid, it is preferable to mix the reaction solution with a basic aqueous solution to decompose and remove the aluminum and subsequently purify.

The olefin polymerization catalyst according to the present embodiment contains, as the central metal of the complex, at least one metal selected from the group consisting of Group 8 elements, Group 9 elements and Group 10 elements. The "Group 8 elements", "Group 9 elements" and "Group 10 elements" used herein are the names based on the IUPAC long periodic table (new periodic table). These elements may sometimes be collectively named as "Group VIII element" based on the short periodic table (old periodic table). More specifically, Group 8 elements, Group 9 elements and Group 10 elements (Group VIII element) are at least one selected from the group consisting of iron, ruthenium, osmium, cobalt, rhodium, iridium, nickel, palladium and platinum.

Among these elements, transition elements are preferable, and specifically, at least one selected from the group consisting of iron, ruthenium, osmium, cobalt, rhodium, iridium, nickel, palladium and platinum is preferable. Further, in light of having a high olefin polymerization activity, at least one selected from the group consisting of iron, cobalt, nickel and palladium is more preferable. Furthermore, in light of a high polymerization activity and availability, at least one selected from the group consisting of nickel and palladium is further preferable.

In the production method of the olefin polymerization catalyst according to the present embodiment, the mixing method of the diimine compound represented by the formula (1) and at least one metal selected from the group consisting of Group 8 elements, Group 9 elements and Group 10 elements is not particularly limited and examples include (i) a method of adding at least one metal salt selected from the group consisting of Group 8 elements, Group 9 elements and Group 10 elements (hereinafter, sometimes simply referred to as "salt") to a solution with the diimine compound dissolved therein and mixing, (ii) a method of mixing a solution with the diimine compound dissolved therein and a solution with the salt dissolved therein and (iii) a method of physically mixing the diimine compound and the salt without using a solvent.

The method for taking out the complex from the mixture of the diimine compound represented by the formula (1) and at least one metal selected from the group consisting of Group 8 elements, Group 9 elements and Group 10 elements is not particularly limited and examples include (a) a method of distilling off a solvent when the solvent is used in the mixture, and separating the solid matter by filtration,
(b) a method of separating the precipitate produced from the mixture by filtration,
(c) a method of purifying the precipitate by adding a poor solvent to the mixture and separating by filtration and
(d) a method of directly taking out the solvent-free mixture.

Subsequently, washing treatment using a solvent capable of dissolving the diimine compound represented by formula (1), washing treatment using a solvent capable of dissolving the metal or recrystallization treatment using a suitable solvent may further be carried out.

Among the above methods, the method of dissolving the diimine compound and the salt using a solvent and mixing (in other words, the methods (i) and (ii)) can form the complex in the system and be directly used as the catalyst, eliminating the necessity of the operation for purifying the produced complex, hence industrially preferable. In other words, the mixtures of (i) and (ii) can also be used directly as the catalysts. Alternatively, it is also feasible to prepare the catalyst by separately adding a solution (or a slurry) of the diimine compound represented by the formula (1) and a solution (or a slurry) of at least one metal selected from the group consisting of Group 8 elements, Group 9 elements and Group 10 elements to a reactor.

Examples of the salt of at least one metal selected from the group consisting of Group 8 elements, Group 9 elements and Group 10 elements include iron(II) chloride, iron(III) chloride, iron(II) bromide, iron(III) bromide, iron(II) acetylacetonate, iron(III) acetylacetonate, iron(II) acetate, iron (III) acetate, cobalt(II) chloride, cobalt(III) chloride, cobalt (II) bromide, cobalt(III) bromide, cobalt(II) acetylacetonate, cobalt(III) acetylacetonate, cobalt(II) acetate, cobalt(III) acetate, nickel 2-ethylhexanoate, nickel(II) chloride, nickel (II) bromide, nickel(II) acetylacetonate, palladium chloride, palladium acetylacetonate and palladium acetate. These salts having a solvent or water may be used. For example, complexes having an organic molecule coordinated such as nickel(II) chloride-dimethoxyethane complex can also be preferably used.

The solvent for allowing the compound represented by the formula (1) to contact the metal is not particularly limited. Both nonpolar solvents and polar solvents can be used. Examples of the nonpolar solvent include hydrocarbon solvents such as hexane, heptane, octane, benzene, toluene, xylene, cyclohexane and methylcyclohexane. Examples of the polar solvent include polar protic solvents such as alcohol solvents and polar aprotic solvents such as tetrahydrofuran. Examples of the alcohol solvent include methanol, ethanol and isopropyl alcohol. Particularly when the mixture is used as the olefin polymerization catalyst, it is preferable to use a hydrocarbon solvent that substantially does not affect the olefin polymerization.

In the olefin polymerization catalyst according to the present embodiment, the content ratio of the diimine compound represented by the formula (1) and at least one metal selected from the group consisting of Group 8 elements, Group 9 elements and Group 10 elements is not particularly limited and the unreacted diimine compound and/or metal may be contained. The ratio of the diimine compound/metal is, in a molar ratio, preferably 0.2/1 to 5/1, more preferably 0.3/1 to 3/1, further preferably 0.5/1 to 2/1. When a ratio of the diimine compound/metal is 0.2/1 or more, the olefin polymerization reaction by the metal to which a ligand is not coordinated can be reduced, thus enabling an intended olefin polymerization reaction to progress selectively. When a ratio of the diimine compound/metal is 5/1 or less, the coordination and the like by excessive ligands is reduced, thus further increasing the activity of the olefin polymerization reaction.

The olefin polymerization catalyst according to the present embodiment can further contain an organoaluminum compound. The organoaluminum compound, in the olefin polymerization reaction, functions as a cocatalyst for further enhancing the catalytic activity of the above complex.

Specific examples of the organoaluminum compound include trim ethyl aluminum, triethylaluminum, tripropylaluminum, triisopropylaluminum, tributylaluminum, triisobutylaluminum, trihexylaluminum, tri octylaluminum, diethylaluminum chloride, ethylaluminum chloride, ethylaluminum sesquichloride and methylaluminoxane. These organoaluminum compounds can be used singly or in combination of two or more.

For methylaluminoxane, a commercial product diluted with a solvent can be used and those wherein trimethylaluminum is partially hydrolyzed in a solvent can also be used. Further, modified methylaluminoxane obtained by allowing trialkylaluminum other than trimethylaluminum such as triisobutylaluminum to coexist at the time of the partial hydrolysis of trimethylaluminum and be co-partially hydrolyzed can also be used. Further, when unreacted trialkylaluminum remains at the time of the above partial hydrolysis, the unreacted trialkylaluminum may be removed by distilling off under reduced pressure. Alternatively, modified methylaluminoxane obtained by modifying methylaluminoxane with an active protic compound such as phenol and derivatives thereof may also be used.

The content ratio of the organoaluminum compound in the olefin polymerization catalyst is not particularly limited. It is preferable for the ratio of the metal in the aluminum/complex in the organoaluminum compound to be, in a molar ratio, 1/1 to 5000/1. When a ratio of the metal in the aluminum/complex in the organoaluminum compound is 1/1 or more, the olefin polymerization reaction progresses more efficiently, whereas, when such a ratio is 5000/1 or less, the production cost can be reduced.

The olefin polymerization catalyst according to the present embodiment may further contain an organozinc compound or an organomagnesium compound in place of or together with the organoaluminum compound. Examples of the organozinc compound include diethylzinc and diphenylzinc. Examples of the organomagnesium compound include methylmagnesium chloride, methylmagnesium bromide, methylmagnesium iodide, ethylmagnesium chloride, ethylmagnesium bromide, ethylmagnesium iodide, (iso)propylmagnesium chloride, (iso)propylmagnesium bromide, (iso) propylmagnesium iodide, phenylmagnesium chloride, phenylmagnesium bromide and phenylmagnesium iodide. These can be used singly or in combination of two or more.

[Second Embodiment: Method for Producing Olefin Oligomer]

The method for producing olefin oligomer according to the second embodiment of the present invention comprises a step of oligomerizing a polymerizable monomer including an olefin in the presence of an olefin polymerization catalyst containing a complex of the ligand being a diimine compound represented by the following formula (1) and at least one metal selected from the group consisting of Group 8 elements, Group 9 elements and Group 10 elements. Note that the olefin polymerization catalyst of the present embodiment is the same as the olefin polymerization catalyst of the first embodiment and the redundant explanation is left out herein.

Examples of the olefin include ethylene and α-olefins. Examples of the α-olefin encompass, in addition to propylene, 1-butene, 1-pentene, -hexene, 1-octene, 1-decene, 1-dodecene, 1-tetradecene, 1-hexadecene and 1-octadecene, those having a branch such as a methyl group at a position other than the second position of the α-olefin such as 4-methyl-1-pentene.

The olefin oligomer obtained by the production method according to the present embodiment may be a homopolymer of one of the above olefins or a copolymer of two or more. It is preferable for the olefin oligomer according to the present embodiment to be, in light of the reactivity, a homopolymer of ethylene or propylene or a copolymer of ethylene and propylene, more preferable to be a homopolymer of ethylene. Further, the olefin oligomer may further contain a structural unit derived from a monomer other than the olefins.

One aspect of the production method according to the present embodiment is a method for introducing the polymerizable monomer to a reactor filled with the olefin polymerization catalyst. The introduction method of the polymerizable monomer to a reactor is not particularly limited and, when the polymerizable monomer is a monomer mixture containing two or more olefins, the monomer mixture may be introduced to a reactor or each of the polymerizable monomers may be introduced separately.

Further, a solvent may be used at the time of oligomerization. Examples of the solvent include aliphatic hydrocarbon solvents such as butane, pentane, hexane, heptane, octane, cyclohexane, methylcyclohexane and decalin; aromatic hydrocarbon solvents such as tetralin, benzene, toluene and xylene. The olefin polymerization catalyst can be dissolved in these solvents to carry out solution polymerization or slurry polymerization. Bulk polymerization can also be carried out using the polymerizable monomer including an olefin as the solvent.

The reaction temperature for the oligomerization is not particularly limited but, for example, it is preferable to range of −20 to 100° C., more preferable to range of −10 to 90° C., further preferable to range of 0 to 80° C. When a reaction temperature is −20° C. or more, the deposition of the produced oligomer can be reduced, whereas, when a reaction temperature is 100° C. or less, the decomposition of the catalyst can be reduced. Furthermore, the reaction pressure is not particularly limited but it is preferable to be 100 kPa to 5 MPa. The reaction time is not particularly limited but it is preferable, for example, to range of 1 minute to 24 hours.

In the present embodiment, the "oligomer" means a polymer having a number average molecular weight (Mn) of 10000 or less. The number average molecular weight of the olefin oligomer obtained by the above production method can be suitably adjusted in accordance with the purpose of use. When the oligomer is used as a wax or a lubricating oil, for example, the number average molecular weight of the oligomer is preferably 300 to 8000, more preferably 400 to 7000.

The Mn of the oligomer can be determined, for example, in terms of polystyrene based on a calibration curve prepared from a standard polystyrene using a GPC apparatus.

According to the production method of the present embodiment, a colorless and clear olefin oligomer can be produced. Thus, the production method according to the present embodiment is useful as the production method of base materials for a lubricating oil such as olefin oligomer waxes, poly α-olefin (PAO).

EXAMPLES

Hereinafter, the present invention is illustrated with reference to Examples, but the following Examples do not intend to limit the present invention.

[Preparation of Ingredients]

Camphorquinone, a solution of trimethylaluminum in toluene and 2-methyl-4-methoxyaniline, products of Tokyo Chemical Industry Co., Ltd., were used as they were. Dimethoxyethane, a dehydrated product of Aldrich, was used as it was. Nickel chloride hexahydrate, product of Wako Pure Chemical Co., Ltd., was used as it was. A nickel chloride dimethoxyethane complex, a product of Aldrich Chemical, was used as it was. Methylaluminoxane, a product of Tosoh Finechem Corporation, TMAO-341, was used as it was. For ethylene, high purity liquefied ethylene, a product of Sumitomo Seika Chemicals, Co., Ltd., dried through molecular sieve 4A was used. For toluene as the solvent, dry toluene, a product of Wako Pure Chemical Industries, Ltd., was used as it was.

[Measurement of the Number Average Molecular Weight (Mn) and the Weight Average Molecular Weight (Mw)]

Two columns (PL gel 10 μm MIXED-B LS) were connected to a high temperature GPC apparatus (a product of Polymer Laboratories Ltd., tradename: PL-220) with refractive index detector. 5 ml of 1-chloronaphthalene solvent was added to 5 mg of a sample and stirred with heating at 220° C. for about 30 minutes. The thus dissolved sample was measured at a flow rate set to be 1 ml/min and a column oven temperature to be 210° C. The molecular weight conversion was carried out based on a calibration curve prepared from a standard polystyrene and a molecular weight in terms of polystyrene was determined.

[Catalytic Efficiency Calculation]

The catalytic efficiency was calculated by dividing the weight of the obtained oligomer by the number of moles of the olefin polymerization catalyst fed.

Production Example 1

Synthesis of Diimine Compound (1-1)

2-Methyl-4-metlioxyaniline (1.276 g, 9.3 mmol, FM=137) was introduced to a 100 ml eggplant flask under a nitrogen atmosphere and dissolved in 20 ml of dry toluene. A solution of trimethylaluminum in toluene (1.8 M, 5.2 ml, 9.3 mmol) was slowly added to the solution and reacted for 2 hours by heating under reflux with toluene. After cooling the reaction solution to room temperature, (1s)-(+)-camphorquinone (0.773 g, 4.7 mmol, FM =166) was added thereto and heated again to reflux for 6 hours.

After completing the reaction, the reaction solution was cooled to room temperature and a 5%-NaOH aqueous solution was added thereto to completely decompose aluminum. The NaOH layer was separated using a separating funnel from the solution thus divided into two layers and the organic layer was washed with brine. The washed toluene solution was dried over anhydrous magnesium sulfate. After filtrating the inorganic substances, the toluene solution was condensed by using an evaporator. The residue was purified by silica gel column chromatography (developing solvent: hexane/ethyl acetate=10/1) to obtain the intended diimine compound (1-1) in a yield of 72%. Note that the purity was confirmed by GC and the peak at MS 404 was also confirmed by GC-MS.

Production Example 2

Synthesis of Diimine Compound (1-2)

The same operation as in the above Synthesis of diimine compound (1-1) was carried out except that 2,4-dimethylaniline (FM=121) was used in place of 2-methyl-4-methoxyaniline to obtain the intended diimine compound (1-2). The peak at MS 372 was confirmed by GC-MS.

Production Example 3

Synthesis of Diimine Compound (1-3)

The same operation as in the above Synthesis of diimine compound (1-1) was carried out except that orthotoluidine (FM=107) was used in place of 2-methyl-4-methoxyaniline to obtain the intended diimine compound (1-3). The peak at MS 344 was confirmed by GC-MS.

Comparative Production Example 1

Synthesis of Diimine Compound (3)

The same operation as in the above Synthesis of diimine compound (1-1) was carried out except that 2,6-diisopropylaniline (FM =177) was used in place of 2-methyl-4-methoxyaniline to obtain the diimine compound (3). The peak at MS 484 was confirmed by GC-MS. The chemical structure of the diimine compound (3) is shown below.

[Chemical Formula 8]

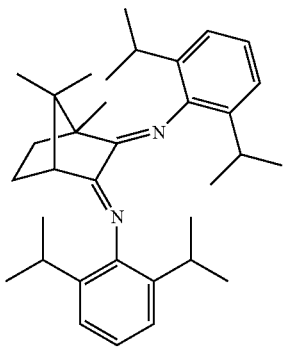

(3)

Example 1

A 660 ml autoclave equipped with an electromagnetic stirrer was thoroughly dried at 110° C. under reduced pressure in advance. Subsequently, dry toluene (80 ml) was introduced into the autoclave under a nitrogen gas stream and a temperature was adjusted to 30° C.

The diimine compound (1-1) (26 µmol) was dissolved in 20 ml of dry toluene in a 50 ml eggplant flask under a nitrogen gas stream. Subsequently, a solution of nickel 2-ethylhexanoate in toluene (amount of nickel 2-ethylhexanoate: 26 µmol), prepared to be 12.6 mM, was introduced to an eggplant flask and stirred for 5 minutes thereby obtaining a solution (A).

A solution of methylaluminoxane in hexane (Al 3.64 M) in a 500 equivalent against to nickel 2-ethylhexanoate was introduced to another 50 ml eggplant flask and the hexane solvent and free trimethylaluminum in the solution were distilled off under reduced pressure. The solution (A) was added to the dried methylaluminoxane and stirred for 5 minutes thereby obtaining a solution (B) containing the olefin polymerization catalyst. The solution (B) was added to an autoclave to which dry toluene was introduced and ethylene, regulated to 0.19 MPa, was continuously introduced at 30° C. The ethylene introduction was halted 15 minutes later, the unreacted ethylene was removed, ethylene in the autoclave was purged with nitrogen. A very small amount of ethanol was added to the autoclave. The autoclave was opened, the content was transferred to a 200 ml eggplant flask and the solvent was distilled off under reduced pressure to obtain 8.84 g of a semi-solid oligomer. The catalytic efficiency was 340 kg Olig/Ni mol. Further, Mn of the obtained oligomer was 870, and Mw was 2100.

Example 2

A 660 ml autoclave equipped with an electromagnetic stirrer was thoroughly dried at 110° C. under reduced pressure in advance. Subsequently, dry toluene (80 ml) was introduced into the autoclave under a nitrogen gas stream and a temperature was adjusted to 30° C.

The diimine compound (1-1) (46 µmol) was dissolved in 20 ml of dry toluene in a 50 ml eggplant flask under a nitrogen gas stream. A solution of nickel 2-ethylhexanoate in toluene (amount of nickel 2-ethylhexanoate: 46 µmol) prepared to be 12.6 mM was added to this solution and stirred for 5 minutes thereby obtaining a solution (C).

A solution of methylaluminoxane in hexane (Al 3.64 M) in a 100 equivalent against to nickel 2-ethylhexanoate was introduced to another 50 ml eggplant flask and the hexane solvent and free trimethylaluminum in the solution were distilled off under reduced pressure. The solution (C) was added to the dried methylaluminoxane and stirred for 5 minutes thereby obtaining a solution (D) containing the olefin polymerization catalyst. The solution (D) was added to the autoclave and ethylene, regulated to 0.80 MPa, was continuously introduced at 30° C. The ethylene introduction was halted 15 minutes later, the unreacted ethylene was removed, ethylene in the autoclave was purged with nitrogen. A very small amount of ethanol was added to the autoclave. The autoclave was opened, the content was transferred to a 200 ml eggplant flask and the solvent was distilled off under reduced pressure to obtain 11.86 g of a semi-solid oligomer. The catalytic efficiency was 258 kg Olig/Ni mol. Further, Mn of the obtained oligomer was 1200 and Mw was 5400.

Example 3

The same operation as in Example 1 was carried out except that the amount of nickel 2-ethylhexanoate added by the solution of nickel 2-ethylhexanoate in toluene was changed to 9.2 µmol in the preparation process of the solution (A) and ethylaluminum sesquichloride (500 equivalent amount) was used in place of methylaluminoxane (500 equivalent amount) in the preparation process of the solution (B). The catalytic efficiency was 189 kg Olig/Ni mol. Further, Mn of the obtained oligomer was 330 and Mw was 360.

Example 4

The same operation as in Example 1 was carried out except that palladium acetate (24 µmop was used in place of the solution of nickel 2-ethylhexanoate in toluene in the preparation process of the solution (A). The catalytic efficiency was 119 kg Olig/Pd mol. Further, Mn of the obtained oligomer was 410 and Mw was 420.

Example 5

The same operation as in Example 3 was carried out except that the diimine compound (1-2) was used in place of the diimine compound (1-1). The catalytic efficiency was 185 kg Olig/Ni mol. Further, Mn of the obtained oligomer was 330 and Mw was 360.

Example 6

The same operation as in Example 3 was carried out except that the diimine compound (1-3) was used in place of the diimine compound (1-1). The catalytic efficiency was 180 kg Olig/Ni mol. Further, Mn of the obtained oligomer was 330 and Mw was 360.

Example 7

A 660 ml autoclave equipped with an electromagnetic stirrer was thoroughly dried at 110° C. under reduced pressure in advance. Subsequently, dry toluene (80 ml) was introduced into the autoclave under a nitrogen gas stream and a temperature was adjusted to 30° C.

Nickel chloride hexahydrate (0.1296 g, 0.55 mmol) was suspended in dry dimethoxyethane (55 ml). 3 ml of the suspension (nickel amount: 2 µmol) was put in a 50 ml eggplant flask and the excess amount of dimethoxyethane was distilled off under reduced pressure. After distillation, 20 ml of dry toluene and a solution of the diimine compound (1-1) (2 µmol) in 10 mM toluene was further added thereto the flask.

Subsequently, methylaluminoxane (100 equivalent amount) was further added to the flask, thereby obtaining a solution containing an olefin polymerization catalyst. The solution was added to the autoclave and ethylene, regulated to 0.19 MPa, was continuously introduced at 30° C. The ethylene introduction was halted 30 minutes later, the unreacted ethylene was removed, ethylene in the autoclave was purged with nitrogen. A very small amount of ethanol was added to the autoclave. The autoclave was opened, the content was transferred to a 200 ml eggplant flask and the solvent was distilled off under reduced pressure to obtain 1.82 g of a semi-solid oligomer. The catalytic efficiency was 910 kg Olig/Ni mol. Further, Mn of the obtained oligomer was 1100 and Mw was 1700.

Example 8

A 660 ml autoclave equipped with an electromagnetic stirrer was thoroughly dried at 110° C. under reduced pressure in advance. Subsequently, dry toluene (80 ml) was introduced into the autoclave under a nitrogen gas stream and a temperature was adjusted to 30° C.

A nickel chloride dimethoxyethane complex (1.2 mg, 5.5 µmol) was added to a 50 ml eggplant flask charged with 20 ml of dry toluene and a solution of the diimine compound (1-1) (5.5 µmol) in 10 mM toluene was further added thereto.

Methylaluminoxane (100 equivalent amount) was further added to the above flask, thereby obtaining a solution containing an olefin polymerization catalyst. The solution was introduced into the autoclave and ethylene, regulated to 0.19 MPa, was continuously introduced at 30° C. The ethylene introduction was halted 30 minutes later, the unreacted ethylene was removed, ethylene in the autoclave was purged with nitrogen. A very small amount of ethanol was added to the autoclave. The autoclave was opened, the content was moved to a 200 ml eggplant flask and the solvent was distilled off under reduced pressure to obtain 0.14 g of a semi-solid oligomer. The catalytic efficiency was 25 kg Olig/Ni mol. Further, Mn of the obtained oligomer was 2300 and Mw was 4000.

Comparative Example 1

The same operation as in Example 1 was carried out except that nickel 2-ethythexanoate was not used. A polymer was not obtained.

Comparative Example 2

The same operation as in Example 1 was carried out except that the diimine compound (3) was used in place of the diimine compound (1-1). Powdery polyethylene was obtained and the catalytic efficiency was 320 kg Olig/Ni mol. Further, Mn of the obtained polyethylene was 110000 and Mw was 165000.

The invention claimed is:
1. An olefin polymerization catalyst containing a complex of a ligand being a diimine compound represented by the following formula (1) and at least one metal selected from the group consisting of Group 8 elements, Group 9 elements, and Group 10 elements:

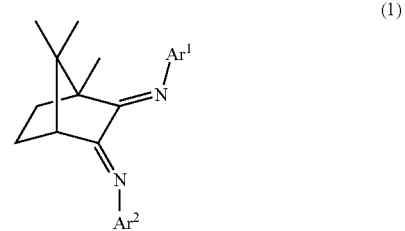

(1)

wherein $Ar^1$ and $Ar^2$ may be the same or different and are respectively a group represented by the following formula (2):

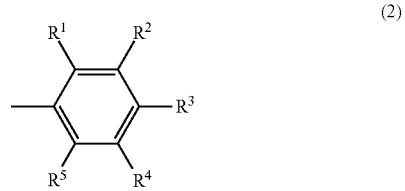

(2)

wherein
$R^1$ is a hydrogen atom and $R^5$ is a hydrocarbyl group having 1 to 5 carbon atoms, and
$R^2$, $R^3$, and $R^4$ may be the same or different and are respectively a hydrogen atom or an electron-donating group.
2. The olefin polymerization catalyst according to claim 1, further containing an organoaluminum compound.

3. A method for producing an olefin oligomer comprising oligomerizing a polymerizable monomer including an olefin in the presence of the olefin polymerization catalyst according to claim 1.

4. A method for producing an olefin oligomer comprising oligomerizing a polymerizable monomer including an olefin in the presence of the olefin polymerization catalyst according to claim 2.

* * * * *